(12) United States Patent
San Mateo et al.

(10) Patent No.: US 6,754,308 B2
(45) Date of Patent: Jun. 22, 2004

(54) METHOD AND SYSTEM FOR MULTI-AXIS BEAMBLOCK TRAY FOR MULTIPLE DEFINING HEADS

(75) Inventors: Ed San Mateo, Pittsburg, CA (US); Rolando R. Tayag, Benicia, CA (US); Salah Captain, Moraga, CA (US); William Gibb, San Anselmo, CA (US); John H. Hughes, Martinez, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 20 days.

(21) Appl. No.: 09/929,713

(22) Filed: Aug. 13, 2001

(65) Prior Publication Data

US 2003/0031297 A1 Feb. 13, 2003

(51) Int. Cl.$^7$ .................................................. H05G 1/54
(52) U.S. Cl. ........................ 378/117; 378/145; 378/147; 378/204
(58) Field of Search .............................. 378/16, 64, 65, 378/117, 145, 147, 148, 156, 157, 203, 204, 205, 150; 250/505.1, 515.1; 600/414, 425, 426, 427; 369/272–291

(56) References Cited

U.S. PATENT DOCUMENTS 5,365,566 A * 11/1994 Maas ........................ 378/150

* cited by examiner

Primary Examiner—Edward J. Glick
Assistant Examiner—Courtney Thomas

(57) ABSTRACT

A beamblock tray for use with multiple defining heads within a medical linear accelerator is disclosed. The beamblock tray comprises a tray portion, and a plurality of coded connectors coupled to the tray portion that make the tray "intelligent" enough to identify its orientation to a user. The tray portion can be inserted into the defining head in a plurality of directions based upon the plurality of coded connectors. A system and method in accordance with the present invention utilizes a plurality of coded connectors that can be used to identify a patient. In addition, the connectors and a mounting flange are such that they permit the tray to be inserted in a plurality of directions. Finally, a coding system is provided that prevents radiation from being delivered if the tray is oriented incorrectly. A dual axis beamblock tray in accordance with the present invention circumvents this problem by a counting for the two possible orientations of beamblock tray holders, thereby permitting the radiation therapist to use a single tray with a variety of linear accelerators.

21 Claims, 2 Drawing Sheets

METHOD AND SYSTEM FOR MULTI-AXIS BEAMBLOCK TRAY FOR MULTIPLE DEFINING HEADS

FIELD OF THE INVENTION

The present invention relates to the field of radiation oncology and more specifically to a beamblock tray that can be used in multiple types of defining heads, and a coding system that ensures proper orientation of the tray.

BACKGROUND OF THE INVENTION

Medical linear accelerators can be used to generate x-ray radiation for the treatment of cancer. While x-ray radiation can help to arrest or reverse the progression of cancer, x-rays are also capable of damaging healthy tissue. Therefore, during the course of radiation therapy, it is important to minimize the amount of radiation delivered to healthy tissue surrounding the cancerous tumor. FIG. 1 is a simple diagram of a medical linear accelerator 10. A defining head 12 is coupled to a supporting gantry 14. The defining head 14 holds an x-ray source 16 which is coupled to a beamblock tray 18. The beamblock tray is coupled to a control console 20 which includes software for providing a particular treatment plan for a patient.

One way to precisely shape the x-ray beam is to mount the beamblock tray 18 in between the x-ray source and the patient. X-ray impermeable shielding (not shown) can be molded into precise shapes and mounted onto the beamblock tray 18. In turn, the beamblock tray 16, together with the shielding, is mounted on the "defining head" of the medical linear accelerator. In this way, x-ray radiation is delivered to the target tissue while minimizing the amount of radiation reaching neighboring tissue. This is a well-established method of shaping the x-ray beam.

FIG. 2 illustrates a conventional beamblock tray 18. The conventional beamblock tray 18 includes a coded connector 102 which is inserted in a slot of the defining head which allows the beamblock tray 18 to be utilized in a particular orientation. Software within the control console 20 (FIG. 1) provides the support for the coding scheme. The coded connector 102 in a preferred embodiment is a resistor pair combination which defines the treatment for a particular patient which is to receive the radiation.

Over the past 20 years, many new features have been introduced into the design of medical linear accelerators. As a consequence of these improvements, it has been necessary to make changes to the defining head, including the orientation of the slots in which the beamblock trays are inserted. As a result, radiation clinics that have been operating linear accelerators for several years may have some linear accelerators with one slot orientation and other linear accelerators with a different slot orientation. This can create a problem when a patient has to be treated on more than one linear accelerator (which might occur because of scheduling constraints, for example). In such cases, the clinic staff must prepare two beamblock trays—one for each slot orientation—to ensure that the beam field is correctly shaped in all of the linear accelerators. The disadvantages of preparing two trays are (a) the cost of the extra beamblock tray, (b) extra preparation time required by the clinical staff, (c) extra material involved in preparing the shielding, and (d) extra storage space for the second tray.

Accordingly, what is needed is a system and method for overcoming the above-identified problems. The present invention addresses such a need.

SUMMARY OF THE INVENTION

A beamblock tray for use with multiple defining heads within a medical linear accelerator is disclosed. The beamblock tray comprises a tray portion, and a plurality of coded connectors coupled to the tray portion The tray portion can be inserted into a defining head in a plurality of directions based upon the plurality of coded connectors.

A system and method in accordance with the present invention utilizes a plurality of coded connectors that can be used to identify a patient. In addition, the connectors and mounting flange are such that permits the tray to be inserted a plurality of directions. Finally, a coding system is provided that prevents radiation from being delivered if the tray is oriented incorrectly. A dual axis beamblock tray in accordance with the present invention circumvents this problem by a counting for the two possible orientations of beamblock tray holders, thereby permitting the radiation therapist to use a single tray with a variety of linear accelerators.

DETAILED DESCRIPTION

The present invention relates to the field of radiation oncology and more specifically to a beamblock tray that can be used in multiple types of defining heads, and a coding system that ensures proper orientation of the tray. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

Figure 3:
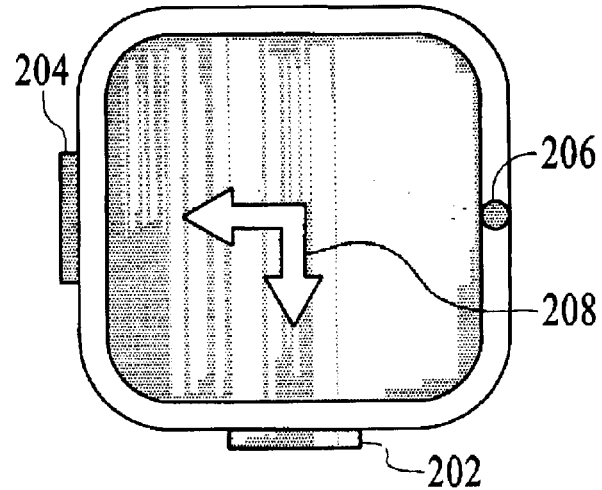
FIG. 3 illustrates a dual-axis beamblock tray in accordance with the present invention.

FIG. 3 illustrates a dual-axis beamblock tray 200 in accordance with the present invention. The tray 200 includes first and second coded connectors 202 and 204 and a flange 206 which surrounds the tray portion 208. There are two primary features that distinguish the tray from conventional beamblock trays. First, a flange is extended around the entire perimeter of the tray portion 208 so that the tray 200 can be inserted into slots within the head (not shown) in either of two directions as indicated by the arrows in FIG. 3. Second, in a preferred embodiment the coded connector 202 is located along the bottom edge of the tray 200 and the connector 204 is located along the left edge of the tray 200. The coded connectors 202 and 204 allow the tray to be "intelligent" enough to identify its orientation to the user.

Although the connectors 202 and 204 are located in the specific positions noted, one of ordinary skill in the art readily recognizes that the connectors 202 and 204 could be in variety of positions and they would be within the spirit and scope of the present invention. In addition, although the preferred embodiment utilizes two connectors, one of ordinary skill in the art further recognizes that any number of connectors could be utilized and they would be within the spirit and scope of the present invention.

Each of the connectors 202 and 204 contain a resistor code that uniquely associates the tray with a particular patient. The software in the console control 20 (FIG. 1) can read these codes to ensure that the correct tray is being used for a given patient.

Thus, these two connectors 202 and 204 allow the tray 200 to be inserted in either of two directions. However, a hazard could be created in that the therapist could insert the tray in the wrong direction for a given treatment head. To guard against this possibility, a new set of resistor codes was introduced for one of the connectors, in this case, connector 204. These codes are recognized only by systems using the more recent slot orientation. To describe this feature in more detail, refer now to the following discussion in conjunction with the accompanying figure.

Figure 1:
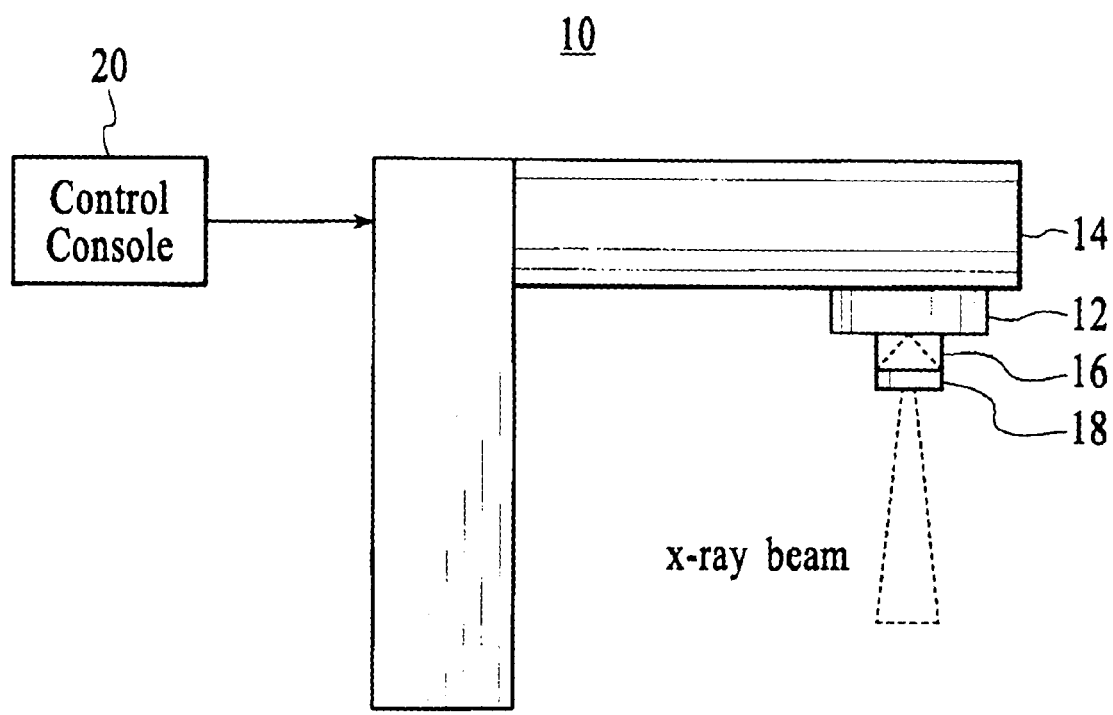
FIG. 1 is a simple diagram of a medical linear accelerator.
Figure 2:
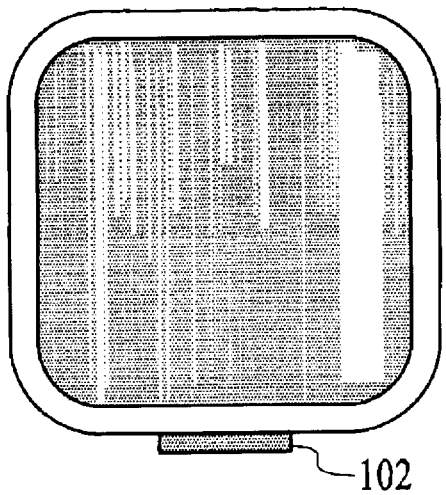
FIG. 2 Illustrates a conventional beamblock tray.
Figure 4:
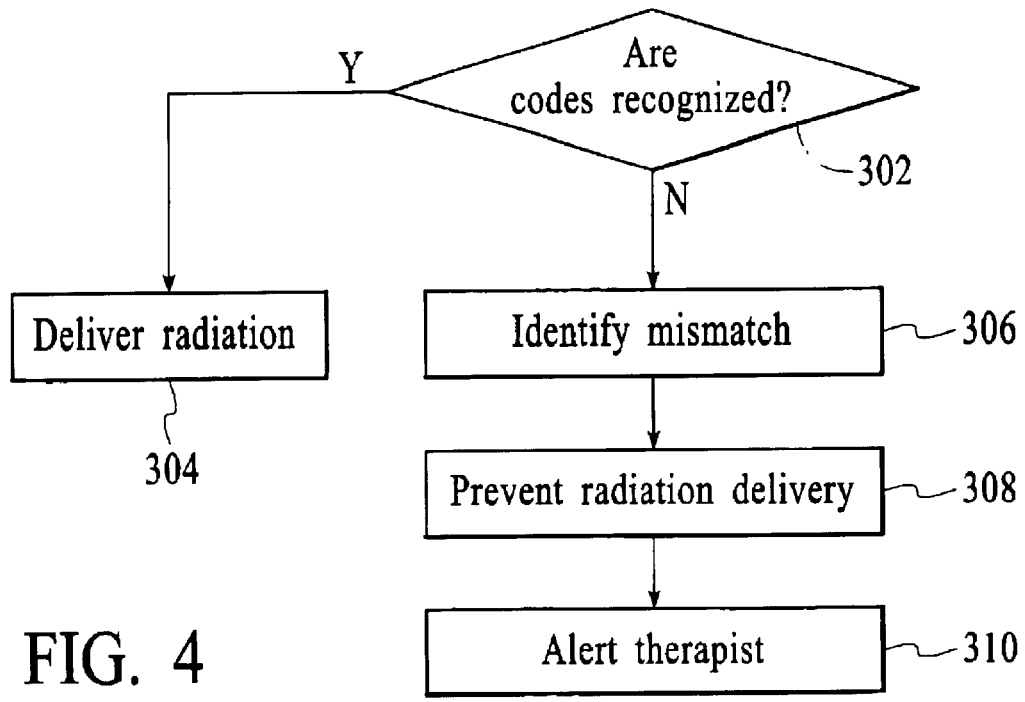
FIG. 4 is a flow chart which which illustrates a process for determining whether the dual axis beamblock tray is oriented correctly.

FIG. 4 is a flow chart which illustrates a process for determining whether the dual axis beamblock tray 200 is oriented correctly. First, it is determined whether the codes are recognized, via step 302. If the codes are recognized then the radiation is delivered, via step 304. If on the other hand, the codes are not recognized, a mismatch is identified, via step 306. Thereafter, radiation is prevented from being delivered, via step 308, and the radiation therapist is alerted, via step 310. In this way, radiation can be delivered only if the tray 200 is properly inserted into the defining head (FIG. 1).

Conclusion

A system and method in accordance with the present invention utilizes a plurality of coded connectors that can be used to identify a patient. In addition, the connectors and mounting flange are such that permits the tray to be inserted in a plurality of directions. Finally, a coding system is provided that prevents radiation from being delivered if the tray is oriented incorrectly. Thereby, the tray is "intelligent" enough to identify its orientation to a user.

A dual-axis beamblock tray in accordance with the present invention circumvents these problems by accounting for the two possible orientations of beamblock tray holders, thereby permitting the radiation therapist to use a single tray with a variety of linear accelerators.

Although the present invention has been described in accordance with the embodiments shown, one of ordinary skill in the an will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A beamblock tray for use with multiple defining heads in a medical linear accelerator, the beamblock tray comprising:
   a tray portion; and
   a plurality of coded connectors coupled to the tray portion, wherein the tray portion can be inserted into a defining head in a plurality of directions based upon the plurality of coded connectors, and wherein each of the plurality of coded connectors allow the tray to be intelligent enough to identify its orientation to a user.

2. The tray of claim 1 which includes a flange which surrounds the tray portion and is coupled between the plurality of coded connectors and the tray portion.

3. The tray of claim 1 wherein the plurality of coded connectors comprise first and second coded connectors.

4. The tray of claim 3 wherein the first coded connector is located along a bottom edge of the tray portion and the second coded connector is located along a left edge of the tray portion.

5. The tray of claim 1 wherein each of the coded connectors is uniquely associated with the tray for a particular patient.

6. A beamblock tray for use with multiple defining heads in a medical linear accelerator, the beamblock tray comprising:
   a tray portion; and
   first and second coded connectors coupled to the tray portion, wherein the tray portion can be inserted into a defining head in a plurality of directions based upon the first and second coded connectors, and a flange which surrounds the tray portion is coupled between the first and second coded connectors and the tray portion, and wherein each of the first and second coded connectors allow the tray to be intelligent enough to identify its orientation to a user.

7. The tray of claim 6 wherein the first coded connector is located along a bottom edge of the tray portion and the second coded connector is located along a left edge of the tray portion.

8. The tray of claim 7 wherein each of the first and second coded connectors comprises a resistor pair.

9. The tray of claim 7 wherein each of the coded connectors is uniquely associated with the tray for a particular patient.

10. A medical linear accelerator comprising:
    a support gantry coupled to a control console in the medical linear accelerator;
    a defining head coupled to the support gantry; and
    a beamblock tray for use with the defining head, the beam block tray comprising a tray portion and a plurality of coded connectors coupled to the tray portion, wherein the tray portion can be inserted into the defining head in a plurality of directions based upon the plurality of coded connectors, and wherein each of the plurality of coded connectors allow the tray to be intelligent enough to identify its orientation to a user.

11. The medical linear accelerator of claim 10 which includes a flange which surrounds the tray portion and is coupled between the plurality of coded connectors and the tray portion.

12. The medical linear accelerator of claim 10 wherein the plurality of coded connectors comprise first and second coded connectors.

13. The medical linear accelerator of claim 12 wherein the first coded connector is located along a bottom edge of the tray portion and the second coded connector is located along a left edge of the tray portion.

14. The tray of claim 10 wherein each of the coded connectors is tray for a particular patient.

15. A method for determining if a beamblock tray is oriented correctly in a defining head of a medical linear accelerator, the method comprising the steps of:
    (a) uniquely associating the tray with a particular patient based on a code;
    (b) determining if a coded connector of a plurality of coded connectors on the beamblock tray is recognized as having the code;
    (c) identifying a mismatch if the coded connector is not recognized; and
    (d) preventing radiation from being delivered by the medical linear accelerator.

16. The method of claim 15 that further includes the step of alerting a radiation therapist if radiation is not delivered.

17. A medical linear accelerator comprising:
    a support gantry coupled to a control console in a medical linear accelerator;

a defining head coupled to the support gantry; and a beam block tray for use with the defining head, the beamblock tray comprising a tray portion and first and second coded connectors coupled to the tray portion, wherein the tray portion can be inserted into a defining head in a plurality of directions based upon the first and second coded connectors, and a flange which surrounds the tray portion is coupled between the first and second coded connectors and the tray portion, and wherein the coded connectors allow the tray to be intelligent enough to identify its orientation to a user.

18. The medical linear accelerator of claim 17 wherein the first coded connector is located along a bottom edge of the tray portion and the second coded connector is located along a left edge of the tray portion.

19. The medical linear accelerator of claim 17 wherein the first and second coded connectors comprises a resistor pair.

20. A computer readable medium containing program instructions for determining if a beamblock tray is oriented correctly in a defining head of a medical linear accelerator, the program instructions for:

(a) uniquely associating the tray with a particular patient based on a code;

(b) determining if a coded connector of a plurality of coded connectors on the beamblock tray is recognized as having the code; and (c) identifying a mismatch if the coded connector is not recognized; and (d) preventing radiation from being delivered by the medical linear accelerator.

21. The computer readable medium of claim 20 which includes program instructions for (d) alerting a radiation therapist if radiation is not delivered.

* * * * *